United States Patent [19]

Vollbrecht et al.

[11] Patent Number: 5,063,077
[45] Date of Patent: Nov. 5, 1991

[54] PROCESS FOR THE REMOVAL OF CHOLESTEROL AND CHOLESTEROL ESTERS FROM EGG YOLK

[75] Inventors: Heinz-Rüdiger Vollbrecht, Altenmarkt; Jan Cully, Trostberg; Johann Wiesmüller, Engelsberg, all of Fed. Rep. of Germany

[73] Assignee: SKW Trostberg Aktiengesellschaft, Trostberg, Fed. Rep. of Germany

[21] Appl. No.: 439,556

[22] Filed: Nov. 21, 1989

[30] Foreign Application Priority Data

Aug. 26, 1989 [DE] Fed. Rep. of Germany ....... 3928258

[51] Int. Cl.$^5$ .......................... A23L 1/32; A23L 1/015
[52] U.S. Cl. ..................................... 426/614; 426/442
[58] Field of Search ............... 426/614, 417, 491, 490, 426/442

[56] References Cited

U.S. PATENT DOCUMENTS

| | | | |
|---|---|---|---|
| 4,290,774 | 9/1981 | Girgis et al. | 436/71 |
| 4,333,959 | 6/1982 | Bracco et al. | 426/614 |
| 4,376,072 | 3/1983 | Connolly | 426/657 |
| 4,880,573 | 11/1989 | Courregelongue et al. | 260/420 |

FOREIGN PATENT DOCUMENTS 0318326  5/1989  European Pat. Off. ............ 426/422

OTHER PUBLICATIONS

O. R. Fennema, "Food Chemistry", 1985, Marcel Dekker, Inc., New York, pp. 837–838, 841–844.

*Primary Examiner*—Donald E. Czaja
*Assistant Examiner*—A. J. Weier
*Attorney, Agent, or Firm*—Felfe & Lynch

[57] ABSTRACT

Cholesterol and cholesterol esters are removed from egg yolk by a process wherein a) optionally after the addition of an emulsion-breaking agent to the egg yolk, the egg yolk plasma is separated from the LDL-granula fraction, b) cholesterol and cholesterol esters which are contained in the egg yolk plasma are adsorbed on a solid adsorption agent and c) the solid material loaded with cholesterol and/or cholesterol esters is separated from the liquid plasma phase and optionally the egg yolk plasma and the separated granula fraction are again mixed together.

8 Claims, No Drawings

PROCESS FOR THE REMOVAL OF CHOLESTEROL AND CHOLESTEROL ESTERS FROM EGG YOLK

FIELD OF THE INVENTION

The present invention is concerned with a multi-step process for the removal of cholesterol and cholesterol esters from egg yolk.

BACKGROUND OF THE INVENTION

Cholesterol and cholesterol esters are lipophilic substances which occur in numerous important foods of animal origin, for example egg yolk, meat, animal fats and the like.

Increased cholesterol levels in the blood serum of humans are regarded as being a risk for arteriosclerosis and of coronary heart disease.

By means of a reduction of the intake of cholesterol by foods, in pathological cases the endeavor is made to achieve the normal cholesterol values in the blood serum again. For that reason, there is a great interest in clearly reducing the content of cholesterol and of cholesterol esters in fat-rich foods of animal origin.

A significant problem is thereby retaining the sensory and nutritional-physiological properties of the foods as much as possible.

Although a number a processes are known for the isolation of cholesterol and of cholesterol esters, these methods are not suitable for the reduction of the cholesterol content of foods since they cause chemical changes in important components of the starting material, for example proteins, triglycerides and the like.

A relatively gentle process which has recently become known uses carbon dioxide high pressure extraction for the removal of cholesterol and of cholesterol esters (cf. V. Krukonis, Supercritical Fluid Processing, International Symposium on Supercritical Fluids, Nice, 1988).

This process is admittedly characterized by the physiological safety of the carbon dioxide used as extraction agent but working at a high pressure is technically rather expensive. Furthermore, with the use of this process unter gentle conditions, cholesterol and cholesterol esters cannot be removed selectively because triglycerides are also extracted at the same time. An improvement of the selectivity by increasing the temperature is, in principle, admittedly possible but this has a negative effect on the loading of the carbon dioxide with cholesterol and cholesterol esters and on the quality of the product obtained.

OBJECT OF THE INVENTION

Therefore, it is an object of the present invention to provide a process for the removal of cholesterol and/or cholesterol esters from egg yolk which does not have the above-mentioned disadvantages of the prior art but rather makes possible a substantially selective reduction of these substances with small technical expenditure and under gentle conditions without impairing the quality of the egg yolk.

DESCRIPTION OF THE INVENTION

Thus, according to the present invention, there is provided a process for the removal of cholesterol and cholesterol esters from egg yolk, wherein a) optionally after the addition of an emulsion-breaking agent to the egg yolk, the egg yolk plasma is separated from the LDL granula fraction, b) cholesterol and cholesterol esters, which are contained in the egg yolk plasma, are adsorbed on a solid adsorption agent and c) the solid material loaded with cholesterol and/or cholesterol esters is separated from the liquid plasma phase and the egg yolk plasma and the separated granula fraction optionally again mixed together.

We have, surprisingly, found that in this way egg yolk products can be obtained with a low cholesterol content and good sensory properties.

In the process according to the present invention, in the first step a fractionation of the egg yolk is carried out in such a manner that the egg yolk plasma is separated from the LDL (low density lipoprotein). This separation step can be carried out by known methods, for example filtration and centrifuging, centrifuging being preferred because it makes possible a particularly quick and effective separation. The centrifuging can be carried out at g forces usual therefor, preferably at 1000 to 10,000 g.

For the better separation of the egg yolk plasma, which makes up about 80 to 85% by weight of the egg yolk, from the granula fraction, it is recommended to add an emulsionbreaking agent in order to improve the separation action and the speed of separation. In the scope of the present invention, there can, in principle, be used all substances permitted by the food laws and regulations which possess emulsion-breaking properties. Water has proven to be specially advantageous because it is cheaply available and can subsequently easily be separated off again. In the case of water, it is sufficient to use it in an amount of from 10 to 600% by weight, especially of from 50 to 100% by weight, referred to the starting weight of the egg yolk, in order to achieve a relatively easy separation.

In the following second step of the process according to the present invention, there takes place the removal of the cholesterol and/or cholesterol esters from the egg yolk plasma by adsorption on an appropriate solid adsorption agent. As adsorption agent, there can be employed the usual non-polar materials, for example active carbon, reverse-phase silica gel and the like. The use of $\beta$-cyclodextrin has proven to be especially advantageous because it makes possible an especially selective adsorption of the cholesterol and cholesterol esters in the presence of the accompanying substances contained in the egg yolk plasma.

The amount of adsorption agent can be varied within wide limits but there is preferably used 3 to 40% by weight of adsorbent, referred to the dry weight of the egg yolk plasma.

During this loading of the adsorbent, which can, be carried out by known methods, for example by simple mixing or stirring, depending on the type and amount of the adsorbent used, about 60 to 99% of the cholesterol and/or cholesterol esters present are removed, whereas the other plasma components remain substantially in the liquid phase.

In the third step of the process according to the present invention, the adsorbent loaded with cholesterol or cholesterol esters is separated from the liquid plasma phase, in which case there can, in principle, be used the technically conventional physical processes and methods for the separation of solid materials from liquids. Because of the rapid and complete separation, it is preferred to use centrifuging. Naturally, however, other separation processes, for example filtration, can also be used.

In general, after desorption of the adsorbed substances, the adsorbent can be used again.

The egg yolk plasma fraction freed in this way from cholesterol and/or cholesterol esters can then be further worked up directly to give egg yolk products. However, for reasons of flavor quality, it is recommended to redisperse in the low-cholesterol plasma fraction the granula fraction which was separated in the first step, which still contains about 10 to 15% of the total cholesterol.

If desired or necessary, the emulsion-breaking agent can be subsequently removed which, in the case of water, can be accomplished by simple spray drying. In this way, depending on the degree or drying, there is obtained liquid egg of an egg yolk powder with a total cholesterol content of about 0.1 to 0.7% which corresponds to an approximately 70 to 90% reduction of the cholesterol content. Because of this good reduction of the cholesterol content combined with the further advantages, such as smaller technical expenditure and good sensory quality of the egg yolk product obtained, the process according to the present invention is especially well suited for carrying out on a technical scale.

The following examples are given for the purpose of illustrating the present invention:

EXAMPLE 1

2 kg. of egg yolk with a total cholesterol content of 1.2% were mixed with distilled water in a weight ratio of 1:1 and centrifuged for 15 minutes at 4° C. and 6000 g. 3.4 kg. of plasma fraction were obtained as supernatant. This was separated from the granula fraction by decanting and then intimately mixed with 238 g. $\beta$-cyclodextrin by stirring for 60 minutes. Thereafter, the loaded $\beta$-cyclodextrin was separated from the liquid plasma phase by centrifuging. As product, there was obtained a plasma fraction with a total cholesterol content of 0.01%. This was again mixed together with the separated granula fraction and worked up by spray drying to give an egg yolk powder with a total cholesterol content of 0.2%, which corresponds to a 90% reduction of the cholesterol in comparison with an untreated egg yolk powder.

EXAMPLE 2

Corresponding to Example 1, 2 kg. of egg yolk were separated by centrifuging into a plasma fraction and a granula fraction. 3.4 kg. of the plasma fraction were subsequently intimately mixed with 170 g. $\beta$-cyclodextrin by stirring for 60 minutes. Thereafter the loaded $\beta$-cyclodextrin was separated from the liquid phase by centrifuging according to Example 1. In this way, there was obtained a plasma fraction with a total cholesterol content of 0.13%. This was mixed with the separated granula fraction and worked up by spray drying to give an egg yolk powder with a total cholesterol content of 0.62%, which corresponds to a 72% reduction of the cholesterol in comparison with an untreated egg yolk powder.

We claim:

1. The method of removing cholesterol and cholesterol esters from egg yolk composed of egg yolk plasma and an LDL-granula fraction, which comprises
   a) optionally adding an emulsion-breaking agent to the egg yolk,
   b) separating the egg yolk plasma from the LDL-granula fraction,
   c) adsorbing the cholesterol and cholesterol esters contained in the egg yolk plasma on a solid adsorbent,
   d) separating the adsorbent loaded with cholesterol and cholesterol esters from the egg yolk plasma, and
   e) optionally recombining the egg yolk plasma with the LDL-granula fraction.

2. The method of claim 1, wherein the separation of the egg yolk plasma from the LDL-granula fraction is effected by centrifuging.

3. The method of claim 1, wherein said emulsion-breaking agent is water.

4. The method of claim 3, wherein the water is used in an amount of 10 to 600% by weight, based on the initial weight of the egg yolk.

5. The method of claim 4, wherein the water is used in an amount of 50 to 100% by weight, based on the initial weight of the egg yolk.

6. The method of claim 1, wherein said adsorbent is $\beta$-cyclodextrin.

7. The method of claim 1, wherein the adsorbent is used in an amount of 3 to 40% by weight, based on the dry weight of the egg yolk plasma.

8. The method of claim 1, wherein the adsorbent loaded with cholesterol or cholesterol esters is separated from the egg yolk plasma by centrifuging.

* * * * *